(12) United States Patent
Wilks (10) Patent No.: US 9,193,652 B2
(45) Date of Patent: Nov. 24, 2015

(54) PHENOL RESIN TREATMENT IMPROVEMENT

(71) Applicant: KELLOGG BROWN & ROOT LLC, Houston, TX (US)

(72) Inventor: Theodor Wilks, Houston, TX (US)

(73) Assignee: KELLOGG BROWN & ROOT LLC, Houston, TX (US)

( * ) Notice: Subject to any disclaimer, the term of this patent is extended or adjusted under 35 U.S.C. 154(b) by 0 days.

(21) Appl. No.: 14/632,133

(22) Filed: Feb. 26, 2015

(65) Prior Publication Data

US 2015/0251984 A1 Sep. 10, 2015

Related U.S. Application Data

(60) Provisional application No. 61/947,746, filed on Mar. 4, 2014.

(51) Int. Cl.
| | |
|---|---|
| *C07C 29/80* | (2006.01) |
| *C07C 37/68* | (2006.01) |
| *C07C 29/76* | (2006.01) |
| *B01D 15/36* | (2006.01) |

(52) U.S. Cl.
CPC ............. *C07C 29/76* (2013.01); *B01D 15/362* (2013.01); *B01D 15/363* (2013.01); *C07C 29/80* (2013.01); *C07C 37/68* (2013.01)

(58) Field of Classification Search
CPC ..................................................... C07C 37/68
USPC ........................................................ 568/754
See application file for complete search history.

(56) References Cited

U.S. PATENT DOCUMENTS

| | | |
|---|---|---|
| 4,308,404 A | 12/1981 | Kwantes et al. |
| 4,358,618 A | 11/1982 | Sifniades et al. |
| 4,359,537 A | 11/1982 | Chong |
| 4,898,995 A | 2/1990 | Knifton et al. |
| 5,015,786 A | 5/1991 | Araki et al. |
| 5,502,259 A | 3/1996 | Zakoshansky et al. |
| 6,066,767 A | 5/2000 | Zakoshansky et al. |
| 6,486,365 B1 | 11/2002 | Fulmer et al. |
| 6,635,789 B2 | 10/2003 | Fulmer et al. |
| 6,825,387 B2 | 11/2004 | Wilks et al. |
| 6,888,035 B2 | 5/2005 | Fallon et al. |
| 7,166,752 B2 | 1/2007 | Marshall, Jr. et al. |
| 7,923,586 B2 | 4/2011 | Stahlbush et al. |
| 2002/0040165 A1 | 4/2002 | Hertzog et al. |
| 2003/0088129 A1 | 5/2003 | Marshall, Jr. et al. |
| 2003/0168329 A1 | 9/2003 | Fulmer et al. |
| 2004/0034256 A1 | 2/2004 | Fallon et al. |
| 2013/0217922 A1 | 8/2013 | Kuechler et al. |

OTHER PUBLICATIONS

Rohm and Haas, Amberlyst A26 OH, Apr. 2001, entire document.

*Primary Examiner* — Elvis O Price
(74) *Attorney, Agent, or Firm* — Gary M. Machetta (57) ABSTRACT

Methods and systems for purifying phenol. The method can include contacting a feed that includes phenol and an aldehyde containing compound with a first ion exchange material to produce a first treated product. The first treated product can have a pH that is less than a pH of the feed. The first treated product can contain less of the aldehyde containing compound than the feed. The first treated product can be contacted with a second ion exchange material to produce a second treated product. The second treated product can have a pH that is greater than the pH of the first treated product. Each of the first ion exchange material and the second ion exchange material can be a solid, a semi-solid, or a combination thereof.

17 Claims, 2 Drawing Sheets

PHENOL RESIN TREATMENT IMPROVEMENT

CROSS-REFERENCE TO RELATED APPLICATION

This application claims priority to U.S. Provisional Patent Application No. 61/947,746, filed Mar. 4, 2014, which is incorporated by reference herein.

BACKGROUND

1. Field

Embodiments described generally relate to methods and systems for purifying phenol containing compositions.

2. Description of the Related Art

Phenol and acetone are produced in various processes, the most common of which are known as the Hock Process, the Hock and Lang Process, and the cumene-to-phenol process, among others. These processes begin with the oxidation of cumene (isopropyl benzene) to form cumene hydro-peroxide ("CHP"). The CHP is then cleaved in the presence of an acid catalyst to form a phenol, acetone, and/or alpha-methyl styrene ("AMS") mixture. The mixture is subsequently neutralized and fractionated to recover the end-products phenol, acetone, and/or AMS.

In the recovered phenol, impurities are removed by contacting the phenol with a cation resin bed to catalyze the impurities into higher boiling components that can be removed by distillation. However, the cation resin bed can result in residual acidity downstream that can catalyze reverse reactions of the higher boiling components under the high distillation temperatures. This residual acidity has been addressed by introducing a caustic solution downstream of the cation resin bed and upstream of the distillation. The addition of the caustic solution, however, results in salt formation that can lead to fouling and reduce product value.

There is a need, therefore, for improved systems and methods for purifying phenol containing compositions.

DETAILED DESCRIPTION

Methods and systems for purifying phenol are provided. The method can include contacting a feed that includes phenol and an aldehyde containing compound with a first ion exchange material to produce a first treated product. The first treated product can have a pH that is less than a pH of the feed. The first treated product can contain less of the aldehyde containing compound than the feed. The first treated product can be contacted with a second ion exchange material to produce a second treated product. The second treated product can have a pH that is greater than the pH of the first treated product. Each of the first ion exchange material and the second ion exchange material can be a solid, a semi-solid, or a combination thereof.

Figure 1:
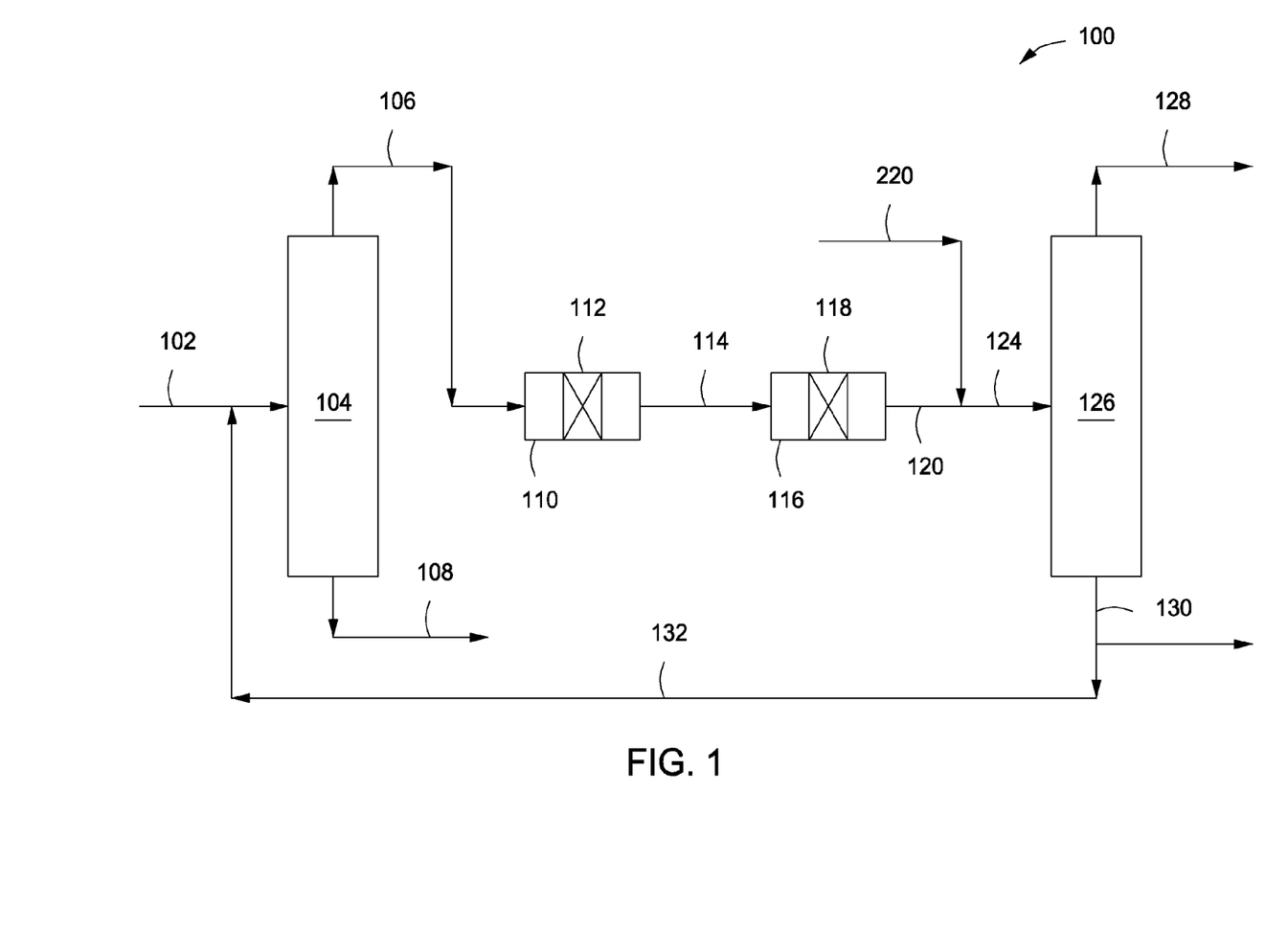
FIG. 1 depicts a schematic of an illustrative purification system for producing phenol, according to one or more embodiments described.

FIG. 1 depicts a schematic of an illustrative purification system 100 for producing phenol, according to one or more embodiments described. Crude phenol via line 102 can be introduced to one or more crude phenol distillation columns (one is shown 104), which can separate at least a portion of any heavier boiling components from the crude phenol to produce a crude phenol overhead via line 106 and a first waste or heavy byproduct via line 108. Depending, at least in part, on the particular configuration of the crude phenol distillation system, the crude phenol can be a distilled overhead (as shown in FIG. 1), a side stream (not shown), and/or a bottoms product stream (not shown). The crude phenol overhead via line 106 can be introduced to one or more first phenol resin treatment units (one is shown 110) to produce a first treated crude product via line 114. As such, although not shown, one or more side-streams can be recovered from the crude phenol distillation column 104 and/or the first waste via line 108 and can be introduced to the first phenol resin treatment unit 110 in lieu of or in addition to the crude phenol overhead in line 106. The first treated crude product via line 114 can have a higher concentration of heavier boiling components than the crude phenol overhead via line 106. The first phenol resin treatment unit 110 can include one or more first ion exchange materials 112. The first ion exchange material 112 can be or include one or more cationic or cation exchange resins. The first treated crude product via line 114 can be introduced to one or more second phenol resin treatment units (one is shown 116) to produce a second treated crude product via line 120. The second phenol resin treatment unit 116 can include one more second ion exchange materials 118. The second ion exchange material 118 can be or include one or more anionic or anion exchange resins. The second treated crude product via line 120 can be mixed or otherwise combined with one or more caustic containing streams via line 220 to produce a mixed crude product via line 124. The mixed crude product via line 124 and/or the second treated crude product via line 120 can be introduced to one or more product columns (one is shown 126) to produce a final or purified phenol product via line 128 and a second waste or heavy byproduct via line 130.

It has been discovered that placing or locating the second ion exchange material 118, such as the anionic exchange resin, downstream of the cationic exchange resin 112 in the synthesis of phenol from the oxidation of cumene can reduce the concentration of the polyatomic ion, sulfate ($SO_4^{-2}$), in the feed to the product column 126. It has also been discovered that placing the second ion exchange material 118, such as the anionic exchange resin, downstream of the cationic exchange resin 112 in the synthesis of phenol from the oxidation of cumene can prolong the service life of the cationic exchange resin 112, lower energy requirements needed for higher carbonyl levels in the feed to the cationic exchange resin 112, and/or reduce salt formation from caustic treatments of the cationic exchange resin 112.

The crude phenol distillation column 104 can include any system, device, or combination of systems and/or devices capable of separating out at least a portion of any components having a higher boiling point than that of phenol that is contained in the crude phenol introduced thereto via line 102. For example, the crude phenol distillation column 104 can be or include one or more distillation columns or fractionation columns. The crude phenol distillation column 104 can be operated at a temperature of at least 120° C. and up to about 225° C., which can vaporize at least a portion of the phenol to separate the phenol from at least a portion of any other impurities such as acetophenone, cumylphenol, dimethylbenzyl alcohol ("DMBA"), alpha methylstyrene dimer, dicumylphenol, and/or any organic compound(s) having a boiling point less than the temperature within the crude phenol distillation column 104.

The crude phenol distillation column 104 can be empty, partially filled, or completely filled with one or more materials to improve mass transfer and/or separation of the water from the crude phenol. For example, the fill material can include, but is not limited to, structured materials, random packed materials, trays, or any combination thereof. Two or more types of fill material can be disposed within the crude phenol distillation column 104. For example, the crude phenol distillation column 104 can contain random dumped packing and one or more trays.

As used herein, the term "trays" can include, but is not limited to, one or more types of trays that can improve the contact between gas and/or liquid phases within the crude phenol distillation column 104. Illustrative trays can include, but are not limited to perforated trays, sieve trays, bubble cap trays, floating valve trays, fixed valve trays, tunnel trays, cartridge trays, dual flow trays, baffle trays, shower deck trays, disc and donut trays, orbit trays, horse shoe trays, cartridge trays, snap-in valve trays, chimney trays, slit trays, or any combination thereof. As used herein, the term "packing material" can include, but is not limited one or more types of structured and/or random shaped material disposed within the crude phenol distillation column 104. The packing material can increase the effective surface area within the crude phenol distillation column 104, which can improve the mass transfer between liquid and/or gas phases within the crude phenol distillation column 104. The packing material can be made of any suitable material, for example metals, non-metals, polymers, ceramics, glasses, or any combination thereof. Illustrative examples of random packing material can include, but are not limited to, Raschig rings, Lessing rings, I-rings, saddle rings, Intalox saddles, Tellerettes, Pall rings, U-rings, or any combination thereof. Illustrative examples of commercially available structured packing can include, but are not limited to, structured packing, corrugated sheets, crimped sheets, gauzes, grids, wire mesh, monolith honeycomb structures, or any combination thereof.

The first phenol resin treatment unit 110 can be or include a vessel having an ion exchange material, such as the cationic exchange resin contained therein. The vessel of the first phenol resin treatment unit 110 can have a plurality of shapes including, but not limited to, a cube, a rectangular box, a cylinder, or some other shape or combination thereof. For example, the vessel can be cylindrical having a longitudinal axis that can be vertically oriented or oriented at an angle with respect to vertical of between about 1°, about 5°, about 10°, about 20°, or about 30° and about 60°, about 70°, or about 80°. In another examples, the vessel can be cylindrical having a longitudinal axis that can be horizontally oriented or oriented at an angle with respect to horizontal of between about 1°, about 5°, about 10°, about 20°, or about 30° and about 60°, about 70°, or about 80°.

The cationic exchange resin bed 112 can include any one or more cationic exchange resins that can catalyze the conversion of aldehyde molecules to heavier components. The cation exchange resin can include one or more H$^+$ functional groups, sulfuric acid, HSO$_4^-$ functional groups, or a mixture thereof. The cationic exchange resins can include, but are not limited to, one or more of the AMBERLYST® ion exchange resins available from Rohm and Haas, one or more of the PUROLITE® CT series ion exchange resins available from the Purolite Company, or any mixture thereof. A suitable cationic exchange resin can be or include cross-linked polystyrene. For example, the cationic exchange resin can be or include a polymer based on a cross-linked styrene divinylbenzene copolymer containing sulfonic acid groups. In another example, the cationic exchange resin 112 can include, but is not limited to, AMBERLYST® 36, PUROLITE® CT-151, or a mixture thereof.

The cationic exchange resin can be solid, semi-solid, or a combination of solid and semi-solid structures. For example, the cationic exchange resin can be in the form of solid particles, semi-solid particles, e.g., a gelled particle, macroporous particles, microporous particles, or any combination thereof. The solid cationic exchange resin can be in the form of pellets, beads, granules, flakes, spheres, cubes, blocks, fibers, filaments, threads, or any combination thereof. As used herein, the terms "semi-solid" and "semi-solid particle" refer to a three-dimensional structure that is insoluble in a particular liquid. The three-dimensional structure can be capable of absorbing and retaining a quantity of the liquid to form a stable, often soft and pliable structure. The cationic exchange resin can be solid and/or semi-solid structures disposed within a fixed bed, a fluid or moving bed, or a combination thereof. In another example, the solid and/or semi-solid structures can be supported on one or more support members such as a rigid support member, between two or more support members such as screens, plates, and the like, or any combination thereof.

The cationic exchange resin can be disposed within a fixed bed. The fixed bed can have a bed depth from a low of about 5 cm, about 10 cm, about 20 cm, about 30 cm, or about 40 cm to a high of about 70 cm, about 85 cm, about 100 cm, about 150 cm, about 200 cm, or about 300 cm or more. The fixed bed containing the cationic exchange resin can be disposed within a contact vessel or "first phenol resin treatment unit 110." The first phenol resin treatment unit 110 can contain or otherwise include one, two, four, six, eight, ten, twelve, fifteen, twenty, or more discrete or separate fixed beds. Any number of first phenol resin treatment units each having any number of fixed beds disposed therein can be arranged in series, parallel, or both with respect to one another. The number of fixed beds, the size of the fixed beds, and the particular cationic exchange resin disposed within each fixed bed can be the same or different between any two first phenol resin treatment units.

The average cross-sectional size or length of the cationic exchange material, e.g., cationic exchange resins, can range from a low of about 0.1 mm, about 0.3 mm, or about 0.5 mm to a high of about 1 mm, about 1.5 mm, about 2 mm, or about 3 mm. The cationic exchange material, e.g., cationic exchange resins, can have an average pore diameter ranging from a low of about 150 Å, about 200 Å, or about 250 Å to a high of about 300 Å, about 400 Å, or about 500 Å. For example, the cationic exchange resin can have an average pore diameter of about 250 Å to about 400 Å, or about 350 Å to about 450 Å, or about 225 Å to about 425 Å. The cationic exchange material, e.g., cationic exchange resins, can have a pore volume ranging from a low of about 0.1 mL/g, about 0.15 mL/g, or about 0.2 mL/g to a high of about 0.25 mL/g, about 0.35 mL/g, or about 0.4 mL/g. For example, the cationic exchange resin can have a pore volume about 0.15 mL/g to about 0.25 mL/g, about 0.2 mL/g to about 0.4 mL/g, or about 0.2 mL/g to about 0.3 mL/g. The cationic exchange material, e.g., cationic exchange resins, can have a surface area ranging from a low of about 10 m$^2$/g, about 15 m$^2$/g, or about 20 m$^2$/g to a high of about 30 m$^2$/g, about 40 m$^2$/g, or about 45 m$^2$/g.

Depending, at least in part, on the particular cationic exchange resin and/or the amount of aldehyde containing compounds present in the crude phenol overhead via line 106, the crude phenol overhead via line 106 can be contacted with the cationic exchange resin at a rate of about 0.5 m$^3$ crude phenol overhead per 1 m$^3$ cationic exchange resin per hour to about 5 m$^3$ crude phenol overhead per 1 m$^3$ cationic exchange resin per hour. For example, the crude phenol overhead via line 106 can be contacted with the cationic exchange resin at a rate from a low of about $0.5\ m^3$, about $0.8\ m^3$, about $1\ m^3$, about $1.3\ m^3$, about $1.5\ m^3$, or about $1.7\ m^3$ to a high of about $2\ m^3$, about $2.5\ m^3$, about $3\ m^3$, or about $4\ m^3$ crude phenol overhead per $1\ m^3$ cationic exchange resin per hour. In another example, the crude phenol overhead via line 106 can be contacted with the cationic exchange resin at a rate ranging from about $2.5\ m^3$ to about $3\ m^3$ crude phenol overhead per $1\ m^3$ cationic exchange resin per hour, from about $2\ m^3$ to about $4\ m^3$ crude phenol overhead per $1\ m^3$ cationic exchange resin per hour, from about $3\ m^3$ to about $5\ m^3$ crude phenol overhead per $1\ m^3$ cationic exchange resin per hour, about $0.5\ m^3$ to about $1.5\ m^3$ crude phenol overhead per $1\ m^3$ cationic exchange resin per hour, or about $2\ m^3$ to about $3.5\ m^3$ crude phenol overhead per $1\ m^3$ cationic exchange resin per hour. The cationic exchange resin can remain in the solid or semi-solid form upon and after contact with the crude phenol overhead via line 106 after refining, purifying, or otherwise processing the crude phenol overhead via line 106.

Depending, at least in part, on the particular cationic exchange material 112, the crude phenol overhead via line 106 can be contacted therewith at a temperature from a low of about 45° C., about 55° C., about 65° C., or about 75° C. to a high of 90° C., about 100° C., about 110° C., about 120° C., or-about 125° C. When the capacity of the cationic exchange resin nears exhaustion, i.e., the cationic exchange resin no longer converts a sufficient amount of aldehyde containing compounds in the crude phenol overhead in line 106, the cationic exchange resin can be replaced with a new cationic exchange material.

In general, the production of phenol from cumene can be represented by reaction scheme I.

(Scheme I)

As depicted in Scheme I, cumene is first oxidized to cumene hydroperoxide and then the cumene hydroperoxide is decomposed under acidic conditions to produce phenol and acetone. Carbonyl-containing byproducts other than acetone, such as aldehyde compounds, can be produced. Illustrative aldehyde compounds can include, but are not limited to acetaldehyde, methyl ethyl ketone, propionaldehyde, or any mixture thereof. These byproducts can complicate the subsequent purification of the phenol. The byproducts can be converted to higher molecular weight products through condensation reactions under acidic conditions. The boiling points of these condensation products are higher than phenol so the phenol can be purified by distillation. The cationic exchange resins can be used in the production of phenol to produce acidic conditions for converting the byproducts to the higher molecular weight products. The cation exchange resins can derive their acidity from sulfonic acid groups. However, release of these sulfonic acid groups can occur from weakly held groups on new resin beds or as the resin ages and begins to breakdown. At the higher distillation temperatures downstream of the resin beds the release of sulfuric acid and/or sulfate can cause decomposition of the high boilers formed in the resin bed to light impurities that affect the phenol product quality. The addition of alkaline neutralizing agents downstream of the cationic exchange resin beds can clog and deteriorate downstream columns and heat-exchanging equipment.

The second phenol resin treatment unit 116 can be or include a vessel having the one or more second ion exchange materials 118, such as the anionic exchange resin, disposed therein. It has been discovered that placing an anionic exchange resin downstream from the cationic exchange resin can reduce a concentration of sulfuric acid and $SO_4^{-2}$ in a phenol stream. The vessel of the second phenol resin treatment unit 116 can have a plurality of shapes including, but not limited to, a cube, a rectangular box, a cylinder, or some other shape or combination thereof. For example, the vessel can be cylindrical having a longitudinal axis that can be horizontally oriented or oriented at an angle with respect to horizontal of between about 1°, about 5°, about 10°, about 20°, or about 30° and about 60°, about 70°, or about 80°. The vessel can also have a longitudinal axis that can be vertically oriented or oriented at an angle with respect to vertical of between about 1°, about 5°, about 10°, about 20°, or about 30° and about 60°, about 70°, or about 80°. The second phenol resin treatment unit 116 or a longitudinal axis of the second phenol resin treatment unit 116 can be at least substantially horizontally oriented. The second phenol resin treatment unit 116 or a longitudinal axis of the second phenol resin treatment unit 116 can be at least substantially vertically oriented.

The anionic exchange resin bed 118 can include any anionic exchange resin that can reduce or eliminate a concentration of $SO_4^{-2}$ in the first treated crude product via line 114. The anionic exchange resins can include, but are not limited to, one or more of the DOWEX® anion exchange resins available from Dow, one or more of the AMBERLYST® anion exchange resins available from Rohm and Haas, one or more of the REILLEX® anion exchange resins available from Vertellus Specialties Inc., one or more of the PUROLITE® aninon exchange resins available from the Puralite Company, or any mixture thereof. A suitable anionic exchange resin can be or include cross-linked polystyrene. For example, the anionic exchange resin can be or include a polymer based on a cross-linked styrene divinylbenzene copolymer. For example, the anion exchange resin 118 can include AMBERLYST® A21, a weak base styrenic resin. Illustrative functional groups that the anion exchange resin 118 can include or have, can be, but are not limited to, primary (R—$NH_2$), secondary (R—NHR'), or tertiary (R—$NR'_2$) amine groups in a free base, $OH^-$, form. Each R and R' can be independently selected from alkyls, cycloalkyls, heterocycloalkyls, aryls, heteroaryls, and substituted aryls. Illustrative primary amines can include, but are not limited to, methylamine and ethylamine. Illustrative secondary amines can include, but are not limited to, dimethylamine and diethylamine. Illustrative tertiary amines can include, but are not limited to, trimethylamine and triethylamine.

The anionic exchange resin can be solid, semi-solid, or a combination of solid and semi-solid structures. For example, the anionic exchange resin can be in the form of solid particles, semi-solid particles, e.g., a gelled particle, macroporous particles, microporous particles, or any combination thereof. The solid anionic exchange resin can be in the form of pellets, beads, granules, flakes, spheres, cubes, blocks, fibers, filaments, threads, or any combination thereof. The anionic exchange resin can be solid and/or semi-solid structures disposed within a fixed bed, a fluid or moving bed, or a combination thereof. In another example, the solid and/or semi-solid structures can be supported on one or more support members such as a rigid support member, between two or more support members such as screens, plates, and the like, or any combination thereof.

The anionic exchange resin can be disposed within a fixed bed. The fixed bed can have a bed depth ranging from a low of about 5 cm, about 10 cm, about 20 cm, about 30 cm, or about 40 cm to a high of about 70 cm, about 85 cm, about 100 cm, about 150 cm, about 200 cm, or about 300 cm or more. The second phenol resin treatment unit 116 can contain or otherwise include one, two, four, six, eight, ten, twelve, fifteen, twenty, or more discrete or separate fixed beds. Any number of second phenol resin treatment units 116 each having any number of fixed beds disposed therein can be arranged in series, parallel, or both with respect to one another. The number of fixed beds, the size of the fixed beds, and the particular anionic exchange resin disposed within each fixed bed can be the same or different between any two second phenol resin treatment units.

The average cross-sectional size or length of the anionic exchange material, e.g., anionic exchange resins, can be from a low of about 0.3 mm, about 0.5 mm, about 0.7 mm, or about 1 to a high of about 1.3 mm, about 1.5 mm, about 1.7 mm, or about 2 mm. The anionic exchange material, e.g., anionic exchange resins, can have an average pore diameter ranging from a low of about 200 Å, about 230 Å, about 250 Å, about 275 Å, or about 300 Å to a high of about 350 Å, about 375 Å, about 400 Å, or about 500 Å. For example, the anionic exchange resin can have an average pore diameter of about 200 Å to about 400 Å, about 240 Å to about 320 Å, about 280 Å to about 380 Å, or about 340 Å to about 460 Å. The anionic exchange material, e.g., anionic exchange resins, can have a pore volume ranging from a low of about 0.1 mL/g, about 0.15 mL/g, or about 0.2 mL/g to a high of about 0.3 mL/g, about 0.35 mL/g, or about 0.4 mL/g. For example, the anionic exchange resin can have a pore volume about 0.15 mL/g to about 0.3 mL/g, about 0.22 mL/g to about 0.34 mL/g, or about 0.26 mL/g to about 0.38 mL/g. The anionic exchange material, e.g., anionic exchange resins, can have a surface area ranging from a low of about 10 m$^2$/g, about 15 m$^2$/g, or about 20 m$^2$/g to a high of about 30 m$^2$/g, about 40 m$^2$/g, or about 50 m$^2$/g.

Depending, at least in part, on the particular anionic exchange resin and/or the amount of $SO_4^{-2}$ in the first treated crude product via line 114, the first treated crude product via line 114 can be contacted with the anionic exchange resin at a rate of about 0.5 m$^3$ first treated crude product per 1 m$^3$ anionic exchange resin per hour to about 5 m$^3$ first treated crude product per 1 m$^3$ anionic exchange resin per hour. For example, the first treated crude product via line 114 can be contacted with the anionic exchange resin at a rate ranging from a low of about 0.5 m$^3$, about 0.7 m$^3$, about 1 m$^3$, or about 2 m$^3$ to a high of about 3 m$^3$, about 4 m$^3$, about 4.5 m$^3$, or about 5 m$^3$ of the first treated crude product per 1 m$^3$ anionic exchange resin per hour. In another example, the first treated crude product via line 114 can be contacted with the anionic exchange resin at a rate ranging from about 2 m$^3$ to about 4 m$^3$ first treated crude product per 1 m$^3$ anionic exchange resin per hour, from about 1.5 m$^3$ to about 3 m$^3$ first treated crude product per 1 m$^3$ anionic exchange resin per hour, from about 3 m$^3$ to about 5 m$^3$ first treated crude product per 1 m$^3$ anionic exchange resin per hour, or about 2.5 m$^3$ to about 3.5 m$^3$ first treated crude product per 1 m$^3$ anionic exchange resin per hour. The anionic exchange resin can remain in the solid or semi-solid form upon and after contact with the first treated crude product via line 114 after refining, purifying, or otherwise processing the first treated crude product via line 114.

Depending, at least in part, on the particular anionic exchange material, the first treated crude product via line 114 can be contacted therewith at a temperature from a low of about 45° C., about 50° C., or about 55° C. to a high of about 60° C., about 70° C., or about 80° C. The first treated crude product in line 114 can be contacted with the anionic exchange material 118 at a temperature less than the crude phenol overhead in line 106 is contacted with the cation exchange material 112.

When the capacity of the anionic exchange resin nears exhaustion, i.e., the anionic exchange resin no longer adsorbs a sufficient amount of acidic compounds from the first treated crude product via line 114, the anionic exchange resin can be replaced with a new anionic exchange material. When the capacity of the anionic exchange resin nears exhaustion, the anionic exchange resin can be regenerated. For example, contacting the first treated crude product via line 114 with the anionic exchange resin can be stopped or diverted elsewhere, e.g., another location containing another anionic exchange resin and one or more regenerate materials can be contacted with the exhausted anionic exchange material. Illustrative regenerate materials can include one or more alkaline solutions. The regenerate material(s) can be liquid, gaseous, or a mixture of liquid and gaseous fluids. For example, the regenerate material(s) can include a solution of sodium hydroxide, sodium phenate, or a mixture thereof.

The second treated crude product via line 120 or the mixed crude product via line 124 can be introduced to the product column 126 to produce the purified phenol product via line 128 and the second heavy byproduct via line 130. The second heavy byproduct in line 130 can be recycled via line 132 to any location upstream of the product column 126. For example, the heavy byproduct via line 132 can be recycled to a location upstream of the crude phenol distillation column 104. As shown, the heavy byproduct via line 132 can be coupled to or otherwise in fluid communication with line 102 such that at least a portion of the heavy byproduct via line 132 can be mixed with the crude phenol via line 102 prior to being introduce to the crude phenol distillation column 104. In another example, at least a portion of the second heavy byproduct in line 130 can be introduced directly to the crude phenol distillation column 104 (not shown) and/or purged from the system 100 via line 132.

The product column 126 can be similar to the crude phenol distillation column 104. For example, the product column 126 can include any system, device, or combination of systems and/or devices capable of separating phenol from at least a portion of the impurities in the mixed crude product thereto via line 124. For example, the product column 126 can be or include one or more distillation columns or fractionation columns. The product column 126 can be empty, partially filled, or completely filled with one or more trays, structured materials, and/or randomly packed materials to improve mass transfer and/or separation of the aniline from the dehydrated product.

Referring to FIG. 1, the crude phenol via line 102 can include, but is not limited to, phenol, acetophenone, cumylphenol, dimethylbenzyl alcohol, alpha methylstyrene dimer, dicumylphenol, or any mixture thereof. The crude phenol overhead in line 106 can include, but is not limited to, phenol, hydroxyl acetone, 2-methylbenzylfuran, acetophenone, or any mixture thereof. The crude phenol overhead in line 106 can have a concentration of phenol from a low of about 99 wt %, about 99.3 wt %, about 99.5 wt %, about 99.6 wt %, or about 99.7 wt % to a high of about 99.8 wt %, about 99.85 wt %, about 99.9 wt %, or about 99.95 wt % The crude phenol overhead in line 106 can have a concentration of hydroxyl acetone from a low of about 0.01 wt %, about 0.02 wt %, or about 0.03 wt % to a high of about 0.05 wt %, about 0.06 wt %, or about 0.07 wt %. The crude phenol overhead in line 106 can have a concentration of 2-methylbenzylfuran from a low of about 0.0001 wt %, about 0.0005 wt %, or about 0.001 wt % to a high of about 0.003 wt %, about 0.004 wt %, or about 0.0050 wt %. The crude phenol overhead in line 106 can have a concentration of acetophenone from a low of about 0.0002 wt %, about 0.0005 wt %, or about 0.001 wt % to a high of about 0.003 wt %, about 0.004 wt %, or about 0.005 wt %.

The crude phenol overhead via line 106 can be introduced to first phenol resin treatment unit 110 to produce the first treated crude product via line 114. The first treated crude product in line 114 can include, but is not limited to phenol, hydroxyl acetone, 2-methylbenzylfuran, acetophenone, or any mixture thereof. The first treated crude product in line 114 can have a concentration of hydroxy acetone from a low of about 0.0001 wt %, about 0.0005 wt %, or about 0.0007 wt % to a high of about 0.001 wt %, about 0.0015 wt %, or about 0.002 wt %. The first treated crude product in line 114 can have a concentration of 2-methylbenzylfuran from a low of about 0.0001 wt %, about 0.0005 wt %, or about 0.0007 wt % to a high of about 0.0009 wt %, or about 0.0010 wt %. The first treated crude product in line 114 can have a concentration of acetophenone from a low of about 0.0002 wt %, about 0.0005 wt %, or about 0.0007 wt % to a high of about 0.001 wt %, about 0.003 wt %, or about 0.0050 wt %. The crude phenol overhead in line 106 can have a pH from a low of about 3, about 4, about 4.5, or about 5 to a high of about 5.5, about 6, about 6.5, about 7, about 7.5, or about 8.

The first treated product in line 114 can have a pH that is less than a pH of crude phenol overhead in line 106. The first treated crude product in line 114 can have a pH from a low of about 2, about 2.5, or about 3 to a high of about 4, about 4.5, or about 5. For example, the first treated crude product in line 114 can have a pH of at least 2, at least 2.2, at least 2.5, at least 2.7, at least 3, or at least 3.3 and less than 5, less than 4.8, less than 4.6, less than 4.4, less than 4.2, less than 4, or less than 3.8. The pH of the first treated crude product can depend, at least in part, on the concentration of the polyatomic ion, sulfate ($SO_4^{-2}$), released from the cationic resin bed. The amount of sulfate ($SO_4^{-2}$) ion in the first treated crude product in line 114 can be from a low of about 0.0002 wt %, about 0.0005 wt %, or about 0.007 wt % to a high of about 0.001 wt %, about 0.003 wt %, or about 0.005 wt %. The first treated product in line 114 can include from a low of about 2 ppm, about 5 ppm, about 10 ppm, or about 15 ppm to a high of about 30 ppm, about 35 ppm, about 40 ppm, about 45 ppm, about 50 ppm, or about 60 ppm of sulfonic acid. For example, the first treated product in line 114 can include at least 3 ppm, at least 7 ppm, at least 12 ppm, at least 18 ppm at least 23 ppm, at least 27 ppm, or at least 33 ppm and up to about 35 ppm, about 40 ppm, about 45 ppm, or about 50 ppm of sulfonic acid.

The first treated crude product via line 114 can be introduced to second phenol resin treatment unit 116 to produce the second treated crude product via line 120. The second treated crude product in line 120 can have a pH that is greater than the pH of the first treated product in line 114. The second treated crude product in line 120 can have a pH from a low of about 4, about 4.3, about 4.7, about 5, about 5.5, or about 6 to a high of about 7, about 7.3, about 7.7, or about 8. In one example, the second treated crude product in line 120 can have a pH of about 4 to less than 7. In another example, the second treated crude product in line 120 can have a pH of greater than 7 and up to about 8. In another example, the second treated crude product in line 120 can have a pH of at least 4, at least 4.4, at least 4.8, at least 5.2, at least 5.7, or at least 6.3 and up to about 6.5, about 6.8, about 7, about 7.2, about 7.6, or about 8. In still another example, the second treated crude product in line 120 can have a pH of about 4, about 4.3, about 4.7, about 5, about 5.5, or about 6 to less than 8, less than 7.7, less than 7.5, less than 7.3, less than 7, less than 6.8, or less than 6.5.

The second phenol resin treatment unit 116 can reduce the concentration of the polyatomic ion, sulfate ($SO_4^{-2}$), in the feed to the product column 126 to less than 0.001 wt %, less than 0.0007 wt %, less than 0.0005 wt %, less than 0.0004 wt %, less than 0.0003 wt %, less than 0.0002 wt %, less than 0.00017 wt %, less than 0.00015 wt %, or less than 0.0001 wt %. The second treated product in line 120 can include less than 15 ppm, less than 12 ppm, less than 10 ppm, less than 7 ppm, less than 5 ppm, less than 4 ppm, less than 3 ppm, less than 2 ppm, or less than 1 ppm of sulfonic acid. The second treated product in line 120 can include less sulfonic acid than the first treated product in line 114.

The second treated crude product via line 120 can be mixed or otherwise combined with the one or more caustic containing streams via line 220 to produce the mixed crude product via line 124. The mixed crude product via line 124 can have a pH from a low of about 4.5, about 4.7, or about 5 to a high of about 5.5, about 6, about 6.5, about 7, about 8, or about 8.5. Alternatively, the second treated crude product via line 120 can be directly introduced to the product column 126. For example, the second treated crude product via line 120 can be introduced to the product column 126 without being combined with the caustic containing stream in line 220. The mixed crude product via line 124 or the crude product via line 124 without the addition of the caustic containing stream 220 can be introduced to the product column 126 to produce the purified phenol product via line 128 and the second heavy byproduct via line 130.

A recycle heavy byproduct via line 130 can be withdrawn from the product column 126 and removed from the system 100 and/or can be recycled via line 132 to any location upstream of the product column 126. In one example, the recycle heavy byproduct via line 132 can be recycled to a location upstream of the crude phenol distillation column 104. For example, line 132 can be coupled to or in fluid communication with line 102 such that the recycle heavy byproduct via line 132 can be mixed with the crude phenol via line 102 prior to being introduce to the crude phenol distillation column 104.

The purified phenol product via line 128 can have a phenol concentration from a low of about 99.7 wt %, about 99.8 wt %, or about 99.85 wt % to a high of about 99.9 wt %, about 99.95 wt %, or about 99.99 wt % or more. For example, the purified phenol product in line 128 can have a phenol concentration of about 99.9 wt % to about 99.95 wt %, about 99.7 wt % to about 99.8 wt %, about 99.85 wt % to about 99.97 wt %, or about 99.9 wt % to about 99.9 wt %. In another example, the purified phenol product in line 128 can have a phenol concentration of at least 99.85 wt %, at least 99.88 wt %, at least 99.9 wt %, at least 99.95 wt %, at least 99.97 wt %, or at least 99.99 wt %. The purified phenol product can have a concentration of impurities of less than 100 ppm, less than 75 ppm, less than 50 ppm, less than 40 ppm, less than 30 ppm, less than 20 ppm, less than 10 ppm, or less than 5 ppm on a dry basis. By maintaining the pH of the second treated crude product in line 120 at or above 4, the purified phenol product in line 128 can have a concentration of impurities of less than 20 ppm, less than 15 ppm, less than 10 ppm, or less than 5 ppm on a dry basis.

Figure 2:
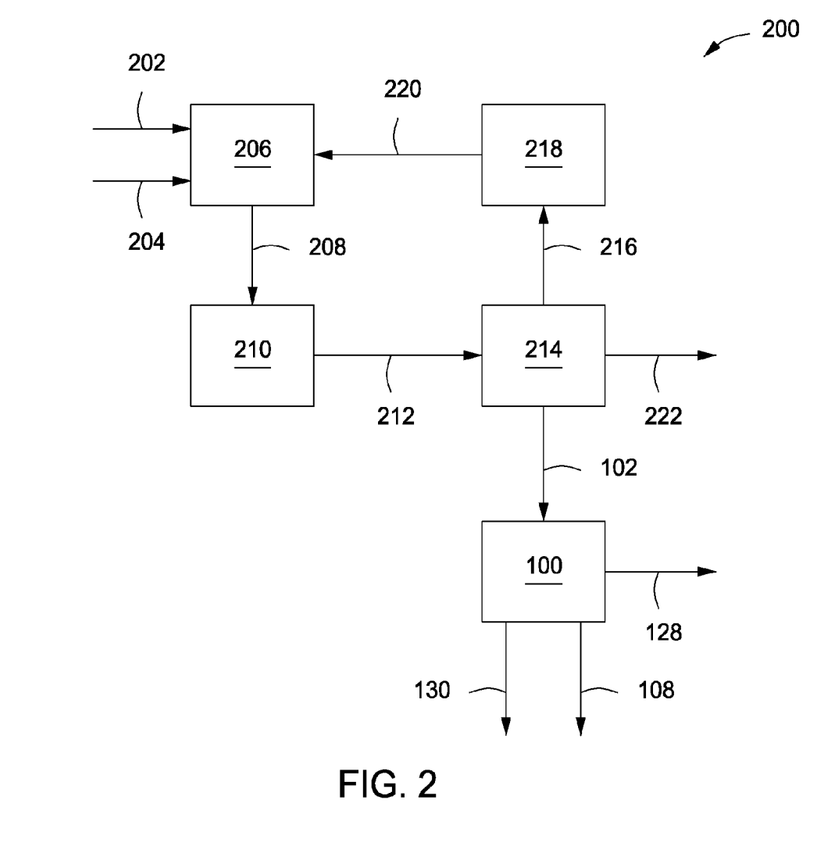
FIG. 2 depicts a schematic of an illustrative system for producing phenol and acetone, according to one or more embodiments described.

FIG. 2 depicts a schematic of an illustrative system 200 for producing phenol and acetone, according to one or more embodiments. A cumene stream via line 202 can be introduced to one or more oxidation and CHP concentration units 206. The cumene stream via line 202 can be subjected to heating in a heat exchanger or other heater (not shown) to produce a heated cumene stream via line 202. Oxygen or any other oxidant via line 204 can be introduced to an oxidation unit of the oxidation and CHP concentration unit 206. For example, the oxidation unit can be or include one or more bubble or cascade columns. Air, oxygen, or other oxygen containing gas can be added to the bottom of the bubble columns, such that oxygen transfers via the air bubbles into the cumene feed, thereby oxidizing the cumene and forming an oxidized product. The oxidized product can include, but is not limited to, cumene hydroperoxide (CHP), dimethylbenzyl alcohol (DMBA), acetophenone (AP), dicumyl peroxide, or any mixture thereof. The oxidized product can include from about 15 wt %, about 20 wt %, or about 23 wt % to about 25 wt %, about 27 wt %, about 30 wt %, or about 35 wt % CHP.

The oxidized product can be introduced to one or more concentration units of the oxidation and CHP concentration units 206 to produce a crude concentrated CHP product via line 208. The concentration unit can be or include one or more vacuum distillation columns, heat exchangers, reflux drums, etc. In such concentration units, cumene can be separated at temperatures below about 105° C., for example. Additional cumene can be added and introduced as reflux to one or more of the vacuum distillation columns to improve cumene separation performance. Further, such additional cumene can be provided for safety, for example, during shutdowns. The cumene obtained from the concentration units can be recycled via line 220 back to the oxidizer to augment the cumene feed introduced via line 202, while the crude concentrated CHP product can be recovered via line 208. The crude concentrated CHP product in line 208 can include from about 80 wt %, or about 81 wt % to about 83 wt %, about 85 wt %, about 90 wt %, or about 93 wt % of CHP.

The crude concentrated CHP via line 208 can be introduced to one or more cleavage units 210. One or more acids can also be introduced to the cleavage unit 210. A suitable acid that can be introduced to the cleavage unit 210 can include, but is not limited to, sulfuric acid. The cleavage unit 210 can include a circulation loop (not shown) with one or more heat exchangers included therein. The crude concentrated CHP can be introduced to the circulation loop and cleaved to produce crude product feed or cleaved product. The crude product feed or cleaved product can include, but is not limited to, acetone, phenol, alpha-methylstyrene, one or more aldehyde containing compounds, or any mixture thereof. The cleavage reaction can be exothermic, thus the heat exchangers can be provided with cooling water or another heat exchange fluid to control the temperature of the concentrated feed in the cleavage unit 210. In the cleavage unit 210, DMBA can be partially dehydrated to AMS, which can react in consecutive reactions with phenol to form cumylphenols. AMS can also form high-boiling point dimers in the cleavage unit 210. DMBA reacts with CHP to form dicumyl peroxide (DCP) and water. Additional byproducts can also be produced, such as hydroxyacetone, 2-methylbenzofuran (2MBF), and diacetone alcohol. These products can be fed to a plug-flow reactor (not shown), for example, at temperatures of about 100° C. or more. In the plug flow reactor, DCP can decompose to AMS, phenol, and acetone. Also in the plug flow reactor, DMBA can be dehydrated to AMS and water. At least a portion of these products can be discharged from the cleavage unit 210 as a crude product feed 212. One example of a cleavage unit can include the cleavage unit discussed and described in U.S. Pat. No. 5,371,305.

The crude product feed via line 212 can be introduced to one or more neutralization units (not shown), where one or more salt solutions, for example, sodium phenate, can reduce, substantially reduce, or terminate any continuing cleavage reactions. At least a portion of the neutralized crude product can be introduced to one or more acetone fractionation units 214. Crude phenol via line 102 can be removed or separated from the neutralized crude product and/or crude product feed via line 212 from the acetone fractionation unit 214 using any suitable process.

The acetone fractionation unit 214 can be in fluid communication with the purification system 100. The acetone fractionation unit 214 can be or include one or more distillation columns, in which acetone via line 222 can be separated as a top product and/or an upper side-stream. The acetone via line 222 can be directed back to the cleavage unit 210 (not shown), can be directed to a storage container or can be otherwise stored or processed for subsequent use. Further, caustic soda or other base, can be added to the acetone fractionation unit 214 to convert aldehydes to high-boiling components.

The purification system 100 can separate and purify the crude phenol via line 102 to produce a purified phenol product via line 128, a first heavy byproduct via line 108 and a second heavy byproduct via line 130, as discussed and disclosed herein. Heavy hydrocarbons via lines 108 and 130 can be removed for further processing, disposal, combustion, etc. Returning to the acetone fractionation unit(s) 214, a hydrocarbon bottoms product from the acetone fractionation unit(s) 214 via line 216 can be directed to the AMS fractionation system 218. In the AMS fractionation system 218, a light hydrocarbon can be recovered, a heavy hydrocarbon can be recovered, and a side-stream mixture of AMS and cumene via line 220 can be recovered.

The side-stream mixture of AMS and cumene can be directed to one or more hydrogenation units (not shown) and mixed with hydrogen. The hydrogenation unit can include a reactor having one or more selective palladium, nickel, or other catalysts therein. The catalysts, in combination with a flow of hydrogen, can cause the AMS to hydrogenate to form cumene. The AMS and cumene mixture can thus be converted to a substantially cumene feed, which can be recycled back to the oxidation unit. A suitable hydrogenation unit can include the hydrogenation units discussed and described in U.S. Pat. No. 7,381,854.

Embodiments described herein further relate to any one or more of the following paragraphs:

1. A method for purifying phenol, comprising: contacting a feed comprising phenol and an aldehyde containing compound with a first ion exchange material to produce a first treated product, wherein the first treated product has a pH that is less than a pH of the feed, and wherein the first treated product contains less of the aldehyde containing compound than the feed; and contacting the first treated product with a second ion exchange material to produce a second treated product, wherein the second treated product has a pH that is greater than the pH of the first treated product, and wherein each of the first ion exchange material and the second ion exchange material is a solid, a semi-solid, or a combination thereof.

2. The method according to paragraph 1, further comprising separating acetophenone, cumylphenol, dimethylbenzyl alcohol, alpha methylstyrene dimer, dicumylphenol, or any combination thereof from a crude phenol to produce the feed.

3. The method according to paragraph 1 or 2, further comprising distilling the second treated product to produce a purified phenol product that contains less than 40 ppm of impurities on a dry basis.

4. The method according to paragraph 3, wherein the impurities comprise acetophenone, cumylphenol, dimethylbenzyl alcohol, alpha methylstyrene dimer, dicumylphenol, or any mixture thereof.

5. The method according to any one of paragraphs 1 to 4, wherein the first ion exchange material comprises a cation exchange resin and the second ion exchange material comprises an anion exchange resin.

6. The method according to paragraph 5, wherein the cation exchange resin comprises sulfuric acid and $HSO_4^-$ functional groups.

7. The method according to paragraph 5, wherein the cation exchange resin comprises a polymer based on a cross-linked styrene divinylbenzene copolymer containing sulfuric acid and $HSO_4^-$ functional groups.

8. The method according to paragraph 5, wherein the anion exchange resin comprises one or more functional groups selected from the group consisting of: primary amine groups, secondary amine groups, and tertiary amine groups, wherein the resin is in a free base, $OH^-$, form.

9. The method according to paragraph 5, wherein the anion exchange resin comprises a polymer based on a cross-linked styrene divinylbenzene copolymer containing quaternary ammonium groups.

10. The method according to any one of paragraphs 1 to 9, wherein the first treated product has a pH of about 2 to about 5, and wherein the second treated product has a pH of about 4 to about 8.

11. The method according to any one of paragraphs 1 to 10, wherein the first treated product comprises about 2 ppm to about 50 ppm sulfonic acid, and wherein the second treated product comprises less than 5 ppm sulfonic acid.

12. The method according to any one of paragraphs 1 to 11, wherein the second ion exchange material has an average pore diameter of about 200 Å to about 500 Å.

13. The method according to any one of paragraphs 1 to 12, wherein the second ion exchange material has a pore volume of about 0.1 mL/g to about 0.4 mL/g.

14. The method according to any one of paragraphs 1 to 13, wherein the second ion exchange material has a surface area of about 10 $m^2$/g to about 50 $m^2$/g.

15. The method according to any one of paragraphs 1 to 14, wherein the first treated product is contacted with the second ion exchange material at a rate of about 0.5 $m^3$ reaction product per 1 $m^3$ ion exchange material per hour to about 5 $m^3$ reaction product per 1 $m^3$ ion exchange material per hour.

16. The method according to any one of paragraphs 1 to 15, wherein the feed is contacted with the first ion exchange material at a temperature of about 45° C. to about 125° C. to produce the first treated product 17. The method according to any one of paragraphs 1 to 16, wherein the first treated product is contacted with the second ion exchange material at a temperature of about 45° C. to about 80° C. to produce the second treated product.

18. The method according to any one of paragraphs 1 to 17, wherein the first treated product is contacted with the second ion exchange material at a temperature less than the feed is contacted with the first ion exchange material.

19. The method according to any one of paragraphs 1 to 18, wherein the aldehyde containing compound comprises acetaldehyde, methyl ethyl ketone, propionaldehyde, or any mixture thereof.

20. A method for producing phenol, comprising: reacting cumene with an oxidant to produce a reaction product comprising cumene hydroperoxide, dimethylbenzyl alcohol, acetophenone, and dicumyl peroxide; separating at least a portion of the dimethylbenzyl alcohol, the acetophenone, the dicumyl peroxide, or any combination thereof from the reaction product to produce a concentrated cumene hydroperoxide product; cleaving the concentrated cumene hydroperoxide product to produce a cleaved product comprising phenol, acetone, alpha methylstyrene, and an aldehyde containing compound; separating at least a portion of the acetone from the cleaved product to produce a first crude phenol product comprising a mixture of phenol, a compound having a boiling point greater than phenol, and aldehyde containing compound; distilling the crude phenol product to produce a first heavy byproduct comprising the compound having a boiling point greater than phenol and a second crude phenol product comprising the phenol and the aldehyde containing compound; contacting the second crude phenol product with a cation exchange material at a temperature of about 45° C. to about 125° C. to produce a first treated product, wherein the first treated product has a pH that is less than a pH of the second crude phenol product, and wherein the first treated product contains less of the aldehyde containing compound than the second crude phenol product; contacting the first treated product with an anion exchange material at a temperature of about 45° C. to about 80° C. to produce a second treated product, wherein the second treated product has a pH that is greater than the pH of the first treated product, and wherein each of the cation exchange material and the anion exchange material is a solid, a semi-solid, or a combination thereof; and distilling the second treated product to produce a purified phenol product and a second heavy byproduct.

21. The method according to paragraph 20, wherein the cation exchange material is a resin comprising sulfuric acid and $HSO_4^-$ functional groups.

22. The method according to paragraph 20 or 21, wherein the anion exchange material is a resin comprising one or more functional groups selected from the group consisting of: primary amine groups, secondary amine groups, and tertiary amine groups, and wherein the resin is in a free base, $OH^-$, form.

23. The method according to any one of paragraphs 20 to 22, wherein the first treated product has a pH of about 2 to about 5 and the second treated product has a pH of about 4 to about 8.

24. The method according to any one of paragraphs 20 to 23, wherein the first treated product comprises about 2 ppm to about 50 ppm sulfonic acid, and wherein the second treated product comprises less than 5 ppm sulfonic acid.

25. The method according to any one of paragraphs 20 to 24, wherein the anion exchange material has an average pore diameter of about 200 Å to about 500 Å.

26. The method according to any one of paragraphs 20 to 25, wherein the anion exchange material has a pore volume of about 0.1 mL/g to about 0.4 mL/g.

27. The method according to any one of paragraphs 20 to 26, wherein the anion exchange material has a surface area of about 10 $m^2$/g to about 50 $m^2$/g.

28. The method according to any one of paragraphs 20 to 27, wherein the aldehyde containing compound comprises acetaldehyde, methyl ethyl ketone, propionaldehyde, or any mixture thereof.

29. The method according to any one of paragraphs 20 to 28, wherein the first treated product is contacted with the anion exchange material at a temperature less than the second crude phenol product is contacted with the cation exchange material.

30. The method according to any one of paragraphs 20 to 29, wherein the purified phenol product contains less than 40 ppm of impurities on a dry basis.

31. The method according to paragraph 30, wherein the impurities comprise acetophenone, cumylphenol, dimethylbenzyl alcohol, alpha methylstyrene dimer, dicumylphenol, or any mixture thereof.

32. A system for purifying phenol, comprising: one or more crude phenol columns configured to separate a crude phenol into a first heavy byproduct and a crude phenol overhead, wherein the crude phenol overhead comprises phenol and an aldehyde containing compound; one or more first phenol resin treatment units configured to contact the crude phenol overhead with a cation exchange material to produce a first treated product that has a pH that is less than the crude phenol overhead and comprises less of the aldehyde containing compound than the crude phenol overhead, wherein the cation exchange material is a solid, a semi-solid, or a combination thereof; and one or more second phenol resin treatment units configured to contact the first treated product with an anion exchange material to produce a second treated product having a pH that is greater than the first treated product, wherein the anion exchange material is a solid, a semi-solid, or a combination thereof.

33. The system according to paragraph 32, wherein the anion exchange material has an average pore diameter of about 200 Å to about 500 Å, a pore volume of about 0.1 mL/g to about 0.4 mL/g, and a surface area of about 10 $m^2/g$ to about 50 $m^2/g$.

34. The system according to paragraph 32 or 33, further comprising one or more product columns configured to separate the second treated product into a second heavy byproduct and a purified phenol product.

Certain embodiments and features have been described using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A method for purifying phenol, comprising:
contacting a feed comprising phenol and an aldehyde containing compound with a first ion exchange material to produce a first treated product, wherein the first treated product has a pH that is less than a pH of the feed, and wherein the first treated product contains less of the aldehyde containing compound than the feed; and
contacting the first treated product with a second ion exchange material to produce a second treated product, wherein the second treated product has a pH that is greater than the pH of the first treated product, and wherein each of the first ion exchange material and the second ion exchange material is a solid, a semi-solid, or a combination thereof.

2. The method of claim 1, further comprising separating acetophenone, cumylphenol, dimethylbenzyl alcohol, alpha methylstyrene dimer, dicumylphenol, or any combination thereof from a crude phenol to produce the feed.

3. The method of claim 1, further comprising distilling the second treated product to produce a purified phenol product that contains less than 40 ppm of impurities on a dry basis.

4. The method of claim 1, wherein the first ion exchange material comprises a cation exchange resin and the second ion exchange material comprises an anion exchange resin.

5. The method of claim 4, wherein the cation exchange resin comprises sulfuric acid and $HSO_4^-$ functional groups.

6. The method of claim 4, wherein the cation exchange resin comprises a polymer based on a cross-linked styrene divinylbenzene copolymer containing sulfuric acid and $HSO_4^-$ functional groups.

7. The method of claim 4, wherein the anion exchange resin comprises one or more functional groups selected from the group consisting of: primary amine groups, secondary amine groups, and tertiary amine groups, wherein the resin is in a free base, $OH^-$, form.

8. The method of claim 4, wherein the anion exchange resin comprises a polymer based on a cross-linked styrene divinylbenzene copolymer containing quaternary ammonium groups.

9. The method of claim 1, wherein the first treated product has a pH of about 2 to about 5, and wherein the second treated product has a pH of about 4 to about 8.

10. The method of claim 1, wherein the first treated product comprises about 2 ppm to about 50 ppm sulfonic acid, and wherein the second treated product comprises less than 5 ppm sulfonic acid.

11. The method of claim 1, wherein the second ion exchange material has an average pore diameter of about 200 Å to about 500 Å, a pore volume of about 0.1 mL/g to about 0.4 mL/g, and a surface area of about 10 $m^2/g$ to about 50 $m^2/g$.

12. The method of claim 1, wherein the first treated product is contacted with the second ion exchange material at a rate of about 0.5 $m^3$ reaction product per 1 $m^3$ ion exchange material per hour to about 5 $m^3$ reaction product per 1 $m^3$ ion exchange material per hour.

13. A method for producing phenol, comprising:
reacting cumene with an oxidant to produce a reaction product comprising cumene hydroperoxide, dimethylbenzyl alcohol, acetophenone, and dicumyl peroxide;
separating at least a portion of the dimethylbenzyl alcohol, the acetophenone, the dicumyl peroxide, or any combination thereof from the reaction product to produce a concentrated cumene hydroperoxide product;

cleaving the concentrated cumene hydroperoxide product to produce a cleaved product comprising phenol, acetone, alpha methylstyrene, and an aldehyde containing compound;

separating at least a portion of the acetone from the cleaved product to produce a first crude phenol product comprising a mixture of phenol, a compound having a boiling point greater than phenol, and aldehyde containing compound;

distilling the crude phenol product to produce a first heavy byproduct comprising the compound having a boiling point greater than phenol and a second crude phenol product comprising the phenol and the aldehyde containing compound;

contacting the second crude phenol product with a cation exchange material at a temperature of about 45° C. to about 125° C. to produce a first treated product, wherein the first treated product has a pH that is less than a pH of the second crude phenol product, and wherein the first treated product contains less of the aldehyde containing compound than the second crude phenol product;

contacting the first treated product with an anion exchange material at a temperature of about 45° C. to about 80° C. to produce a second treated product, wherein the second treated product has a pH that is greater than the pH of the first treated product, and wherein each of the cation exchange material and the anion exchange material is a solid, a semi-solid, or a combination thereof; and distilling the second treated product to produce a purified phenol product and a second heavy byproduct.

14. The method of claim 13, wherein the cation exchange material is a resin comprising sulfuric acid and $HSO_4^-$ functional groups.

15. The method of claim 13, wherein the anion exchange material is a resin comprising one or more functional groups selected from the group consisting of: primary amine groups, secondary amine groups, and tertiary amine groups, and wherein the resin is in a free base, $OH^-$, form.

16. The method of claim 13, wherein the first treated product has a pH of about 2 to about 5 and the second treated product has a pH of about 4 to about 8.

17. The method of claim 13, wherein the first treated product comprises about 2 ppm to about 50 ppm sulfonic acid, and wherein the second treated product comprises less than 5 ppm sulfonic acid.

* * * * *